(12) United States Patent
Kozloski et al.

(10) Patent No.: US 11,532,086 B2
(45) Date of Patent: Dec. 20, 2022

(54) SYSTEMS AND METHODS TO FACILITATE DETERMINATION OF INTERACTION BETWEEN MEDICATIONS AND THE BRAIN USING A BRAIN MEASURE AND A BRAIN MODEL

(71) Applicant: International Business Machines Corporation, Armonk, NY (US)

(72) Inventors: James R Kozloski, New Fairfield, CT (US); Viatcheslav Gurev, Bedford Hills, NY (US); Tuan Minh Hoang Trong, New York City, NY (US); Adamo Ponzi, Scarsdale, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 391 days.

(21) Appl. No.: 16/796,131

(22) Filed: Feb. 20, 2020

(65) Prior Publication Data
US 2021/0264603 A1    Aug. 26, 2021

(51) Int. Cl.
*G06T 7/00* (2017.01)
*G16H 10/60* (2018.01)
(Continued)

(52) U.S. Cl.
CPC ......... *G06T 7/0016* (2013.01); *A61B 5/4848* (2013.01); *A61B 5/7275* (2013.01);
(Continued)

(58) Field of Classification Search
CPC ......... G06T 7/0016; G06T 2207/10088; G06T 2207/20081; G06T 2207/20084;
(Continued)

(56) References Cited

U.S. PATENT DOCUMENTS

2009/0292180 A1    11/2009  Mirow
2016/0210749 A1     7/2016  Nguyen et al.
(Continued)

FOREIGN PATENT DOCUMENTS

KR    101898575 B1    9/2018

OTHER PUBLICATIONS

Salehinejad et al., "Synthesizing Chest X-Ray Pathology for Training Deep Convolutional Neural Networks," in IEEE Transactions on Medical Imaging, vol. 38, No. 5, pp. 1197-1206, May 2019.
(Continued)

*Primary Examiner* — Ping Y Hsieh
*Assistant Examiner* — Daniella M. DiGuglielmo
(74) *Attorney, Agent, or Firm* — Amin, Turocy & Watson, LLP

(57) ABSTRACT

Systems and methods that facilitate determining interaction between medications and the brain using a brain measure and a brain model. Hidden nervous system states are difficult to predict, diagnose, and treat with therapeutic medications. A Dual Neural Machine Translation (d-NMT) algorithmic system that utilizes sets of parameters for a relapsing-remitting MS model based on patient medical records and adjusts a method of parameterization to produce a model that can match patients' medical records and medical images. These parameters are can be used by a therapeutic determining model to recommend therapies, doses, and time courses accurately.

20 Claims, 10 Drawing Sheets

(51) Int. Cl.
    *G16H 30/40*     (2018.01)
    *G16H 50/20*     (2018.01)
    *G06N 3/04*     (2006.01)
    *A61B 5/00*     (2006.01)

(52) U.S. Cl.
    CPC ........... *G06N 3/0454* (2013.01); *G16H 10/60* (2018.01); *G16H 30/40* (2018.01); *G16H 50/20* (2018.01); *G06T 2207/10088* (2013.01); *G06T 2207/20081* (2013.01); *G06T 2207/20084* (2013.01); *G06T 2207/30016* (2013.01)

(58) Field of Classification Search
    CPC ........ G06T 2207/30016; A61B 5/4848; A61B 5/7275; G06N 3/0454; G06N 3/0472; G06N 3/08; G16H 10/60; G16H 30/40; G16H 50/20; G16H 20/10; G16H 50/50
    See application file for complete search history.

(56) References Cited

U.S. PATENT DOCUMENTS

2018/0225823 A1*   8/2018   Zhou .................. G06N 3/084
2020/0364864 A1*  11/2020  Shanbhag ............. G06T 7/0014

OTHER PUBLICATIONS

Xia et al., "Dual Inference for Machine Learning." Proceedings of the Twenty-Sixth International Joint Conference on Artificial Intelligence (IJCAI-17).

Guibas et al., "Synthetic Medical Images from Dual Generative Adversarial Networks." Submitted on Sep. 6, 2017 (v1), last revised Jan. 8, 2018 (this version, v3)), https://arxiv.org/abs/1709.01872.

Lao et al., "Leveraging Disease Progression Learning for Medical Image Recognition." (Submitted on Jun. 26, 2018 (v1), last revised Sep. 1, 2018 (this version, v2)) https://arxiv.org/abs/1806.10128.

Yi et al., "Generative Adversarial Network in Medical Imaging: A Review." (Submitted on Sep. 19, 2018), https://arxiv.org/abs/1809.07294.

Shin et al., "Medical Image Synthesis for Data Augmentation and Anonymization using Generative Adversarial Networks." (Submitted on Jul. 26, 2018 (v1), last revised Sep. 13, 2018 (this version, v2)), https://arxiv.org/abs/1807.10225.

Jing et al., "On the Automatic Generation of Medical Imaging Reports," (Submitted on Nov. 22, 2017 (v1), last revised Jul. 20, 2018 (this version, v3)), https://arxiv.org/abs/1711.08195.

Stretka, "Think of Multiple Sclerosis as a Leaking Swimming Pool [Video]: A new way of looking at the neurodegenerative disorder could lead to more and better treatments" Scientific American, Neurological Health, Jun. 18, 2015.

Xia et al., "Dual Learning for Machine Translation" arXiv.1611.00179v1.

* cited by examiner

SYSTEMS AND METHODS TO FACILITATE DETERMINATION OF INTERACTION BETWEEN MEDICATIONS AND THE BRAIN USING A BRAIN MEASURE AND A BRAIN MODEL

TECHNICAL FIELD

The subject disclosure relates generally to system(s) and method(s) that illustrate determining interaction between medication(s) and the brain using a brain measure and a brain model.

SUMMARY

The following presents a summary to provide a basic understanding of one or more embodiments of the invention. This summary is not intended to identify key or critical elements, delineate scope of particular embodiments or scope of claims. Its sole purpose is to present concepts in a simplified form as a prelude to the more detailed description that is presented later. In one or more embodiments described herein, systems, computer-implemented methods, apparatus and/or computer program products facilitate generation of efficient artificial intelligence to determine an interaction between medications and the brain using a brain measure and a brain model.

In accordance to an embodiment, a system, comprises a processor, operatively coupled to a memory, that executes the following computer executable components: a dual-neural machine translation algorithmic component that trains parameterization of a generative model by receiving sequences of medical records described by a disease progression model and translates the sequences of medical records to an illustrative sequence of corresponding images, wherein the training is performed using the following computer executable components: a medical record prediction component that predicts a first future patient state and first medical record from a first sequence of medical records; a medical image prediction component that predicts a second future patient state and first medical image from a first sequence of medical images; and a pathophysiological component that generates a pathophysiological simulation of a third future patient state using a second sequence of medical images given a first set of parameters wherein a first parameter reflects a population of patients that have presented a first type of medical record.

In accordance with an embodiment, a computer implemented method, comprises: using a processor, operatively coupled to a memory, to execute computer executable components to perform the following acts: using the processor to train parameterization of a generative model by receiving sequences of medical records described by a disease progression model and translates the sequences of medical records to an illustrative sequence of corresponding images, wherein the training is performed by: using the processor to predict a first future patient state and first medical record from a first sequence of medical records; using the processor to predict a second future patient state and first medical image from a first sequence of medical images; and using the processor to generate a pathophysiological simulation of a third future patient state using a second sequence of medical images given a first set of parameters wherein a first parameter reflects a population of patients that have presented a first type of medical record.

DETAILED DESCRIPTION

Figure 1:
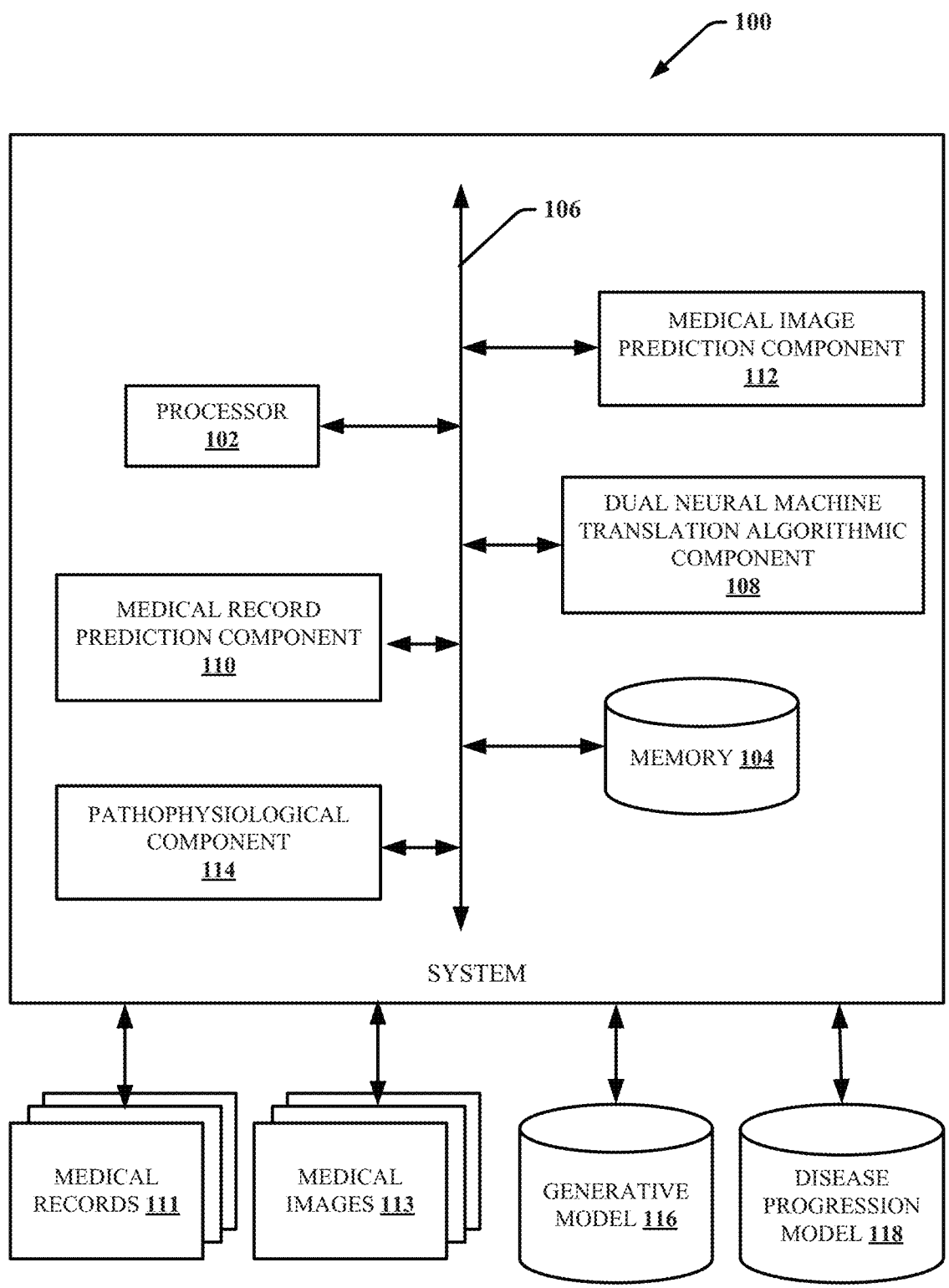
FIG. 1 illustrates a block diagram of an example system implemented that can determine an interaction between medications and the brain using a brain measure and a brain model.

The following detailed description is merely illustrative and is not intended to limit embodiments and/or application or uses of embodiments. Furthermore, there is no intention to be bound by any expressed or implied information presented in the preceding Summary section, or in the Detailed Description section. One or more embodiments are now described with reference to the drawings, wherein like reference numerals are used to refer to like elements throughout. In the following description, for purposes of explanation, numerous specific details are set forth in order to provide a more thorough understanding of the one or more embodiments. It is evident; however, in various cases, that the one or more embodiments can be practiced without these specific details.

The subject disclosure relates generally to system(s) and method(s) that illustrate determining interaction between medication(s) and the brain using a brain measure and a brain model. Embodiments disclosed herein propose use of a Dual Neural Machine Translation (d-NMT) system to set parameters of a model of relapsing-remitting multiple sclerosis (MS) based on patient medical records, and adjust method of parameterization to produce a model that can match patients' medical records and medical images. The resulting parameters of an optimized patient-specific model are not observable directly in the patient and are then used to determine therapies, dosages, and time courses for treatment.

In today's digital world, use of artificial intelligence (AI) has increased exponentially. AI simulates human intelligence processes by machines such as computer systems. These processes include learning wherein the information is acquired, reasoning wherein the information is used to reach approximate conclusions and lastly, self-correction. AI is progressing rapidly from SIRI to self-driving cars. AI can be categorized as weak AI (narrow AI) or strong AI (general AI). Weak AI is designed to perform a narrow task such as facial recognition, driving a car, performing surgery and many virtual technical advancements such as Apple's SIRI. Strong AI is designed to work on unfamiliar tasks where with human cognitive abilities, it can find a solution without human intervention. Thus, AI makes it possible for machines to learn from experience, adjust to new inputs and perform human-like tasks. In comparison with cognitive computing, AI discovers patterns in big data to learn and reveal hidden information or deliver solutions to complex problems. AI is used in many applications such as automation, speech recognition, machine learning, robotics, and machine vision. AI is the main subject in today's technological advancement because it automates repetitive learning and discovery through data analysis and adds intelligence, adapts through progressive learning algorithms, achieves accuracy and produces accurate results. AI has made its way in major application areas such as banking, healthcare, retail, education, and manufacturing. In particular, Artificial Intelligence brings a paradigm shift to healthcare by increasing availability of healthcare data and facilitating rapid progression of analytics techniques.

Artificial intelligence (AI) can make use of various types of structured and unstructured healthcare data. Applications in healthcare provide personalized medicines and X-ray readings. Some popular AI techniques include machine learning methods for structured data, such as the classical support vector machine and neural network. Modern deep learning and natural language processing are other techniques used for unstructured data. Machine learning uses a statistical technique to fit models to data and learn by training the models with the data. It is the most common form used in AI wherein predicting the treatment that is likely to succeed on a patient based on various patient attributes and treatment context. This is called supervised learning such that machine learning and precision medicine applications use a training dataset for which the outcome variable is known. Moreover, the neural network is one of the complex forms of machine learning. It is used to categorize applications by determining whether a patient can acquire a particular disease. It views the inputs, outputs and weights the variables that associate inputs with the outputs, and analyze the problem further. The neural network model with many levels is also known as deep learning that predicts the outcome. One of the common applications of deep learning in healthcare is to recognize potential cancerous lesions in radiology images. Deep learning is also used for radionics to detect features in imaging data beyond what can be perceived by the human eye. Radionics and deep learning are commonly used in oncology-oriented image analysis. This combination provides greater accuracy during the diagnosis process.

The use of AI particularly in healthcare industry provides improvements in patients outcome and reduces costs as companies apply machine learning to make faster and accurate diagnoses than humans. Various technologies in the market can understand natural language and are capable of responding to questions asked. These systems can analyze patient data and other available data sources to form a hypothesis, which is presented to the patient based on predictive analysis theory. Also, other programs are used online to answer questions and assist customers to help schedule follow-up appointments or to help patients through a billing process. There are virtual health assistants that provide basic medical feedback and set reminders for medications. Thus, the healthcare industry evolves around machine learning and artificial intelligence is becoming more ubiquitous. The healthcare industry discovers areas of patient care that require improvement by promptly obtaining patient insights. Many algorithms are outperforming radiologists at spotting malignant tumors and analyzing other diseases in various fields such as for example as neurology and cardiology. Thus, AI capabilities can unleash a full potential of data to improve patient's health and solve health care challenges. This evolution can enable health care organizations to empower physicians with accurate diagnostics and provide targeted prevention capabilities. It can also improve operational performance by optimizing resources and reduce the number of hospital readmissions.

In the healthcare industry, a major area of study is focused on use of artificial intelligence (AI) in neurological disease prevention, diagnosis, prognosis and recovery which has unparalleled advantage over human doctors. Neurological disorders are diseases of the central and peripheral nervous system; this mainly consists of the brain, spinal cord, cranial nerves, peripheral nerves, nerve roots, autonomic nervous system, neuromuscular junction, and muscles. These disorders include epilepsy, Alzheimer's disease, and other dementias, cerebrovascular diseases including stroke, migraine, and other headache disorders, multiple sclerosis, Parkinson's disease, neuroinfectious, brain tumors, traumatic disorders of the nervous system due to head trauma, and neurological disorders as a result of malnutrition. Multiple sclerosis, in particular, is classified as an autoimmune disease of the central nervous system. It is the most common disease course characterized by clearly defined attacks of new or increasing neurologic symptoms. These attacks are called relapses or exacerbations. These relapses are followed by a period of partial or complete recovery. During this recovery period, many symptoms may disappear or continue to become permanent. However, there is no apparent progression of the disease during a remission period. The problem of choosing a therapeutic regimen for a given disease state, its origin, and its likely progression is widespread in the treatment of neurological disorders. Specifically, finding markers for particular conditions, how it arises and how it might change over time is considered as a main factor when choosing treatments for relapsing-remitting multiple sclerosis (RR-MS) and in neurodegenerative disorders in general. Thus, in these embodiments, a technique is described to make use of a dual neural machine translation (d-NMT) algorithmic core to train parameterization of a generative model that employs sequences of medical records described by a disease progression model and translate these into an illustrative sequence of corresponding medical images. The need to illustrate medicine's current understanding of causes and progression to patients in the space of medical imaging is useful since patients understand these lesions to be correlated with more troubling symptoms.

Hidden nervous system states are difficult to predict, diagnose, and treat with therapeutic medications. In particular, multiple sclerosis (MS) states are responsible for flare-ups among patients suffering from the relapsing-remitting form of disease (RR-MS). These are not detectable using standard medical imaging, and therefore are difficult to assign a therapeutic agent, dosage, and time course. Models have been proposed to illustrate how these hidden states evolve, manifest on brain images, and lead to debilitating patient MS symptoms. One such model is the leaking swimming pool model in which hidden states are illustrated as mounds that grow and shrink at different points in a swimming pool at various pool depths. Because the level of water in the pool is also changing, the model explains how multiple factors contribute to manifestation of symptoms and medical image markers (such as lesions) in relapsing-remitting MS. Thus, these embodiments propose use of a Dual Neural Machine Translation (d-NMT) system to set parameters of this model of relapsing-remitting MS based on the patient medical records, and adjust method of parameterization to produce a model that can match patients' medical records and medical images. The resulting parameters of the optimized patient-specific model are not observable directly in the patient and are then used to determine therapies, dosages, and time courses for treatment.

FIG. 1 illustrates a block diagram of an example system 100 that can access data and process that data using variable computing components depicted in accordance with one or more embodiments described herein. The system 100 can facilitate a process of assessing and identifying a large amount of various forms of data. The system 100 can also generate predictive recommendations to an individual level resulting in a context in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Repetitive description of like elements employed in one or more embodiments described herein is omitted for sake of brevity.

System 100 can optionally include a server device, one or more networks and one or more devices (not shown). The system 100 can also include or otherwise be associated with at least one processor 102, operatively coupled to a memory 104, that executes computer executable components. The system 100 can further include a system bus 106 that can couple various components including, but not limited to, a dual neural machine translation (d-NMT) algorithmic component 108 that trains parameterization of a generative model, a medical record prediction component 110 that predicts a subsequent patient state and medical record from a sequence of medical records 111, a medical image prediction component 112 predicts a subsequent patient state and medical image from a sequence of medical images 113, a pathophysiological component 114 generates a sequence of medical images given a set of parameters wherein a parameter reflects a population of patients to have presented a type of medical record and an interpreter component 117 (FIG. 2) that generates a sequence of medical records given a set of parameters wherein a parameter reflects a population of patients to have presented a type of medical image.

In an implementation, the dual-neural machine translation algorithmic component 108 trains parameterization of a generative model 116 by receiving the sequences of medical records 111 described by a disease progression model 118 and translates the sequences of medical records 111 to an illustrative sequence of corresponding images. A generative model can learn data distribution(s) using unsupervised learning towards learning true data distribution of a training set so as to generate new data points with some variations. But it is not always possible to learn exact distribution of data either implicitly or explicitly. Accordingly, it is desirable to try to model a distribution which is as similar as possible to a true data distribution. For example, neural networks can be employed to learn a function which can approximate a model distribution to a true distribution. Two commonly used and efficient approaches are Variational Autoencoders (VAE) and Generative Adversarial Networks (GAN). VAE aims at maximizing a lower bound of data log-likelihood and GAN aims at achieving an equilibrium between Generator and Discriminator. Disease progression modeling involves utilization of mathematical functions as quantitative descriptors of time course of disease status. Disease progression models may incorporate biomarkers of disease severity and/or clinical outcomes to characterize natural progression of disease. In clinical pharmacology, disease models are often integrated with pharmacokinetic-pharmacodynamic models in order to quantify influence of medication treatment on disease progression.

The training is facilitated by the medical record prediction component 110 that predicts a future patient state (i.e. prognosis and medical record) from a sequence of medical records. The medical image prediction component 112 predicts a future patient state (i.e. prognosis and medical image) from a sequence of medical images. The pathophysiological component 114 generates a pathophysiological simulation of a patient state (i.e. illustrative medical images) using a given set of parameters which reflects the predicted prognosis from component 110.

Figure 2:
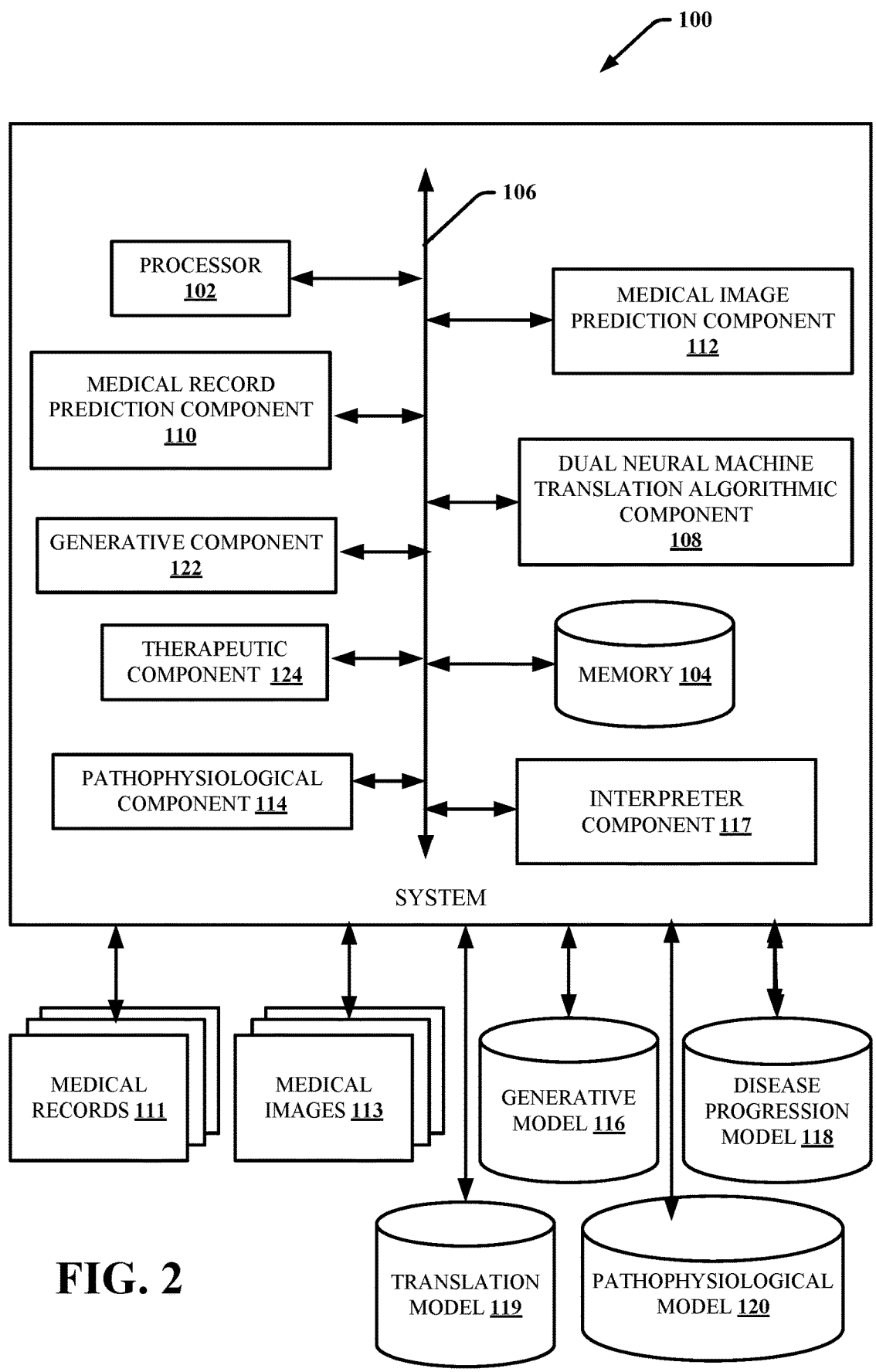
FIG. 2 illustrates a block diagram of an example system implemented that can determine interaction between medications and the brain using a brain measure and a brain model.

Turning to FIG. 2, in an embodiment, the interpreter component 117 generates a prognosis and medical record given a second set of parameters which reflects a patient's medical images. The generative model 116 is a medical record generator that converts the received medical images back to a corresponding medical record. A translation model 119 interprets a sequence of medical records described by the generative model 116 and translates this sequence of medical records into the illustrative sequence of corresponding medical images.

Figure 6:
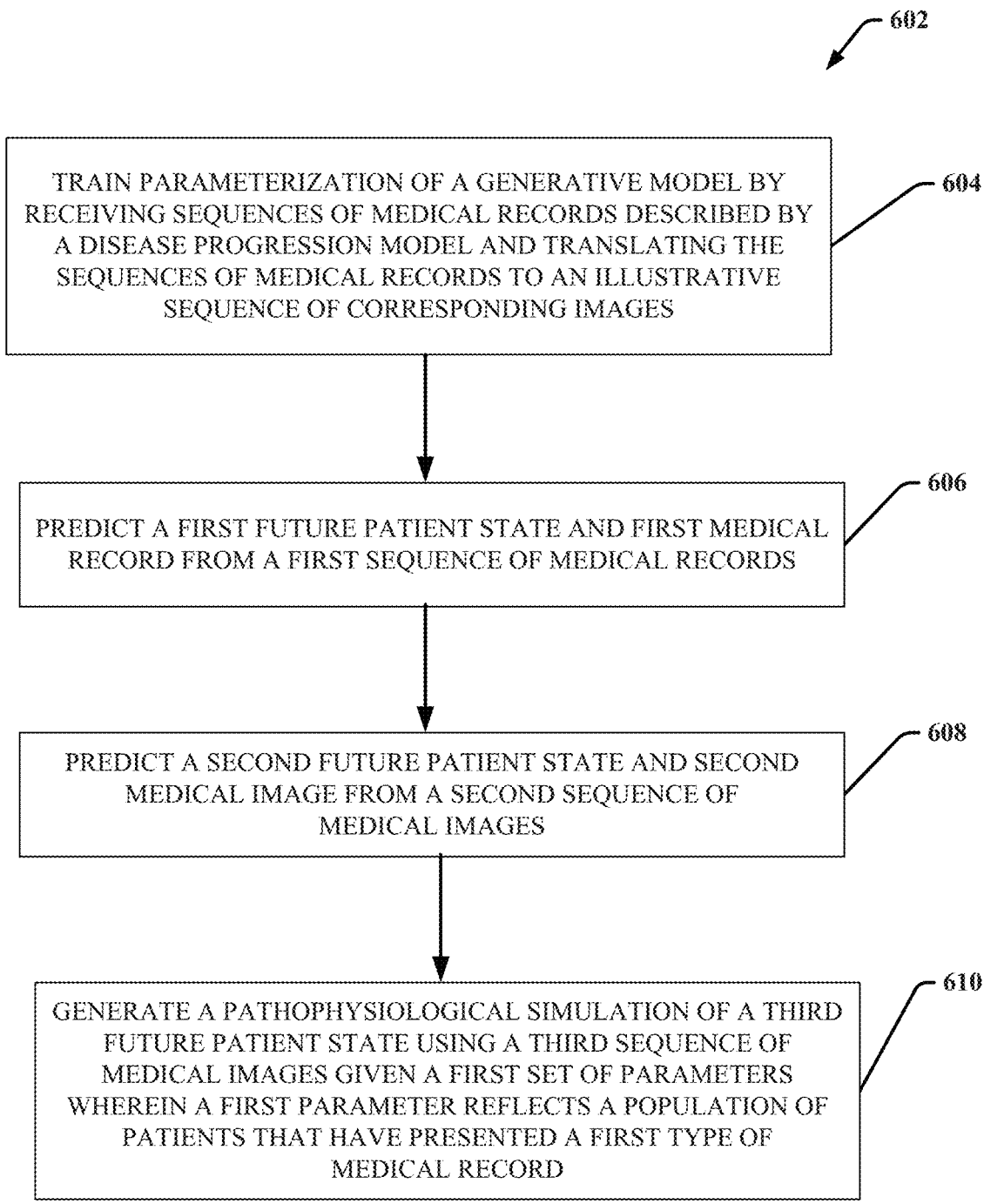
FIG. 6 illustrates an example flowchart of an implementation of a dual neural machine translation (d-NMT) algorithm in accordance with one or more implementations described herein.

In an implementation, the training is facilitated using a pathophysiological model 120 that comprises a leaking swimming pool model (See FIG. 6 and associated description infra.). In an embodiment, the system 100 includes a generative component 122 that employs a second set of parameters to impute patient medical record measurements that were not considered in an evaluation and generates a follow-up notification on these records to assist with therapeutic endpoint measures (e.g., a notification can be sent to a physician to perform such follow-up). The generative component 122 can select records based on learned parameters of a reinforcement learning algorithm by quality of a forward medical image sequence and round-trips. The system 100 can also include a therapeutic component 124 that uses parameters optimized for a patient from a set of generative models as inputs to therapy, dose, and time course selection.

System 100 can be any suitable computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the systems 100 and/or any other suitable device that can employ information provided by system 100. It is to be appreciated that systems 100, components, models or devices can be equipped with communication components (not shown) that enable communication between the system, components, models, devices, etc. over one or more networks.

The various components of systems 100 can be connected either directly or via one or more networks. Such networks can include wired and wireless networks, including, but not limited to, a cellular network, a wide area network (WAN) (e.g., the Internet), or a local area network (LAN), non-limiting examples of which include cellular, WAN, wireless fidelity (Wi-Fi), Wi-Max, WLAN, radio communication, microwave communication, satellite communication, optical communication, sonic communication, or any other suitable communication technology. Moreover, the aforementioned systems and/or devices have been described with respect to interaction between several components. It may be appreciated that such systems and components can include these components or sub-components specified therein, some of the specified components or sub-components, and/or additional components. Sub-components may also be implemented as components communicatively coupled to other components rather than included within parent components. Further yet, one or more components and/or sub-components can be combined into a single component providing aggregate functionality. The components can also interact with one or more other components not specifically described herein for the sake of brevity, but known by those of skill in the art.

The subject computer processing systems, methods apparatuses and/or computer program products can be employed to solve new problems that arise through advancements in technology, computer networks, the Internet and the like.

Modelling the underlying pathophysiological causes and dynamics has been attempted in relapsing-remitting multiple sclerosis (RR-MS) using the leaking swimming model, but not with a formal translational aspect from medical records to simulated medical images. By formalizing this relationship, optimal parameters can be chosen which can capture the pathophysiological causes of disease (e.g., reserve capacity or inflammation vulnerability of a patient captured by the water depth parameter). The model may then be elaborated to include causes that include the real-world targets of medications. Doctors have used ad hoc mental models and dynamic illustrations such as the leaking swimming pool model to adjust by trial and error treatments until the patient state and imaging results respond to the therapy. In many neurodegenerative diseases, the pathophysiological causes of RR-MS are still debated, though clear markers (pale lesions) during advanced flare-ups do appear on medical images. The need, therefore, to identify the hidden mechanistic relationships between symptoms and brain imaging markers exist and may hold as the main factor to determine therapies. Thus, these embodiments mainly focus on relapsing-remitting multiple sclerosis (RR-MS) and neurodegenerative disorders in general and provide an algorithm to suggest therapeutic treatments for these diseases effectively. Illustrative AI pertains to a class of AI wherein a learning mechanism, such as the dual neural machine translation (d-NMT) system, is used to learn a set of parameters which are simply black box hidden parameters of a learning system. These embodiments also use a mechanistic modeling component wherein models of tissues (e.g., heart and brain tissues) are designed such that these tissue models have parameters that are not arbitrary black box parameters, but instead correspond to physiological and pathophysiological features of tissue system components (e.g., myocytes, neurons, myofilaments, and ion channels). Together, these black box and mechanistic models are intended to perform function approximation and sample the distribution of pathophysiological features (e.g., mechanistic model parameters) coherent with the distributions of patient observations (e.g., medical records, medical images) used to train the learning system. Also, samples of parameters may then be used as parts of an equation to represent real pathophysiological prophecies, including cellular, tissue and medically relevant processes that are not yet grounded in a tissue.

Figure 3:
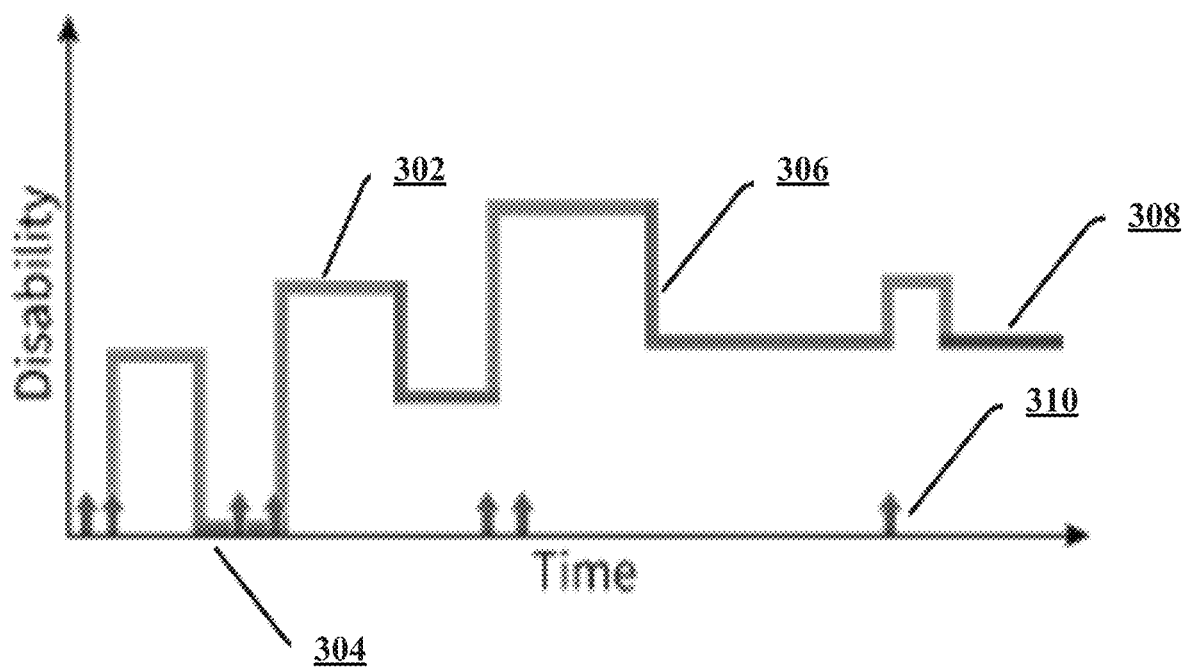
FIG. 3 illustrates an example graph of disease activities that can occur in relapsing-remitting multiple sclerosis (RR-MS).

FIG. 3 illustrates an example graph of disease activities that can occur in relapsing-remitting multiple sclerosis (RR-MS). Relapsing-remitting MS is defined by inflammatory attacks on myelin as well as the nerve fibers. RR-MS can further be characterized into active with relapses of new magnetic resonance imaging (MRI) activity, not active, and worsening. An increased infirmity is confirmed when the person exhibits the same level of infirmity at the next scheduled neurological evaluation. Following a relapse, as denoted by block 302, the new symptoms may disappear without causing any increase in the level of infirmity as denoted by block 304. On the other hand, the new symptoms may only partially disappear and thus cause an increase in infirmity as denoted by block 306. New lesions on MRI, as denoted by block 310, often occur as part of a relapse. However, new MRI lesions indicating multiple sclerosis (MS) activity may also occur without symptoms of which the person is aware of. The patient's condition may also be stable without any activity as denoted by block 308. Some processes to diagnose MS is by medical history and neurological exam. MRI evoked potentials and occasionally lumbar puncture tests may be used to confirm when MS is suspected. When MS is diagnosed, evidence of disease activity separated in time (lesions that formed at different points in time) and space is observed. However, the process of diagnosis is time taking and no one test can be used to diagnose MS. Thus, the diagnosis of MS is conducted by eliminating potential causes of symptoms.

Figure 4:
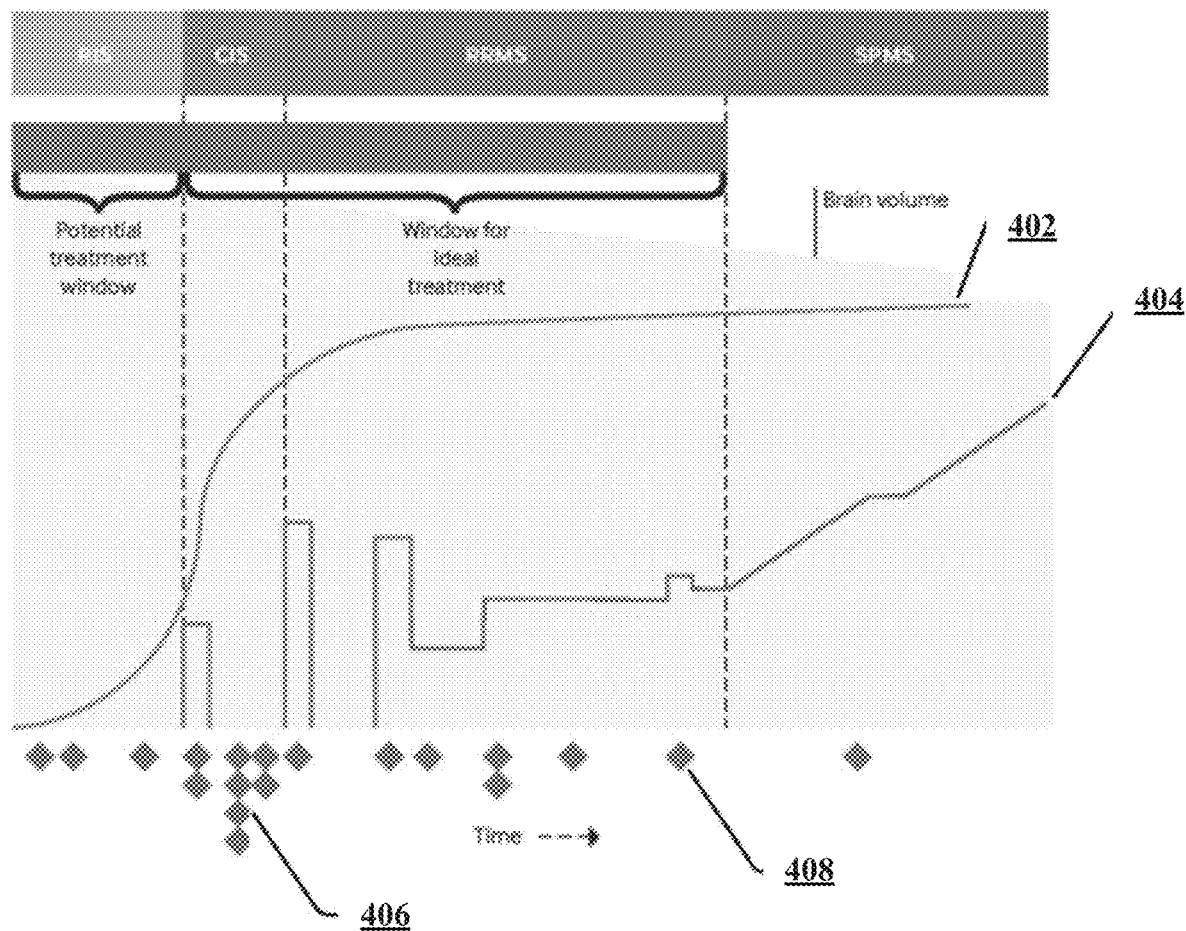
FIG. 4 illustrates an example graph of a common time course for relapsing-remitting multiple sclerosis (RR-MS) flare-up.

FIG. 4 illustrates an example graph of a common time course for relapsing-remitting multiple sclerosis flare-ups. Finding markers for a particular condition, how it has arisen and how it might change over time is considered as a main factor when choosing treatments for relapsing-remitting multiple sclerosis (RR-MS) and in any neurodegenerative disorders in general. Common time course of RR-MS flare-ups, plotted in terms of brain imaging markers by an MRI lesion burden is denoted at 402. The infirmity also known as symptomatology over time, with time windows indicating when therapy can be administered is denoted at 404. The window may correspond to a specific medication or medication dose and multiple such windows might exist for an entire range of therapeutic options. MRI activity is performed from time to time as per the treatment window as denoted at 406. Upon some period of time, MRI activity with relapse occurs as shown at 408. Many tests can be performed to diagnose RR-MS and based on the symptoms and physical examination, MRI imaging tests can look for demyelinating lesions on the brain and spinal cord. In many neurodegenerative diseases, the pathophysiological causes of RR-MS are still debated, though clear markers (pale lesions) during advanced flare-ups do appear on medical images. In these embodiments, a mechanistic model is used for MS wherein it can represent the pathophysiological mechanism. These embodiments intend to use these mechanistic model's parameters and identify the interaction of the medication with the brain by using model output to generate samples from the distribution of patient observations (e.g., medical records, medical images). Hence, the problem of choosing a therapy is alleviated by these embodiments by informing which marker in the patient's data indicates a particular therapeutic course or another based on the response of the pathophysiological mechanism to a modeled medication provided to the mechanistic model. These embodiments leverage black-box model for patient categorization which can categorize observations of a patient undergoing an acute lesion incident. That category is visible in the MRI and that is known as MRI lesion burden. As the patient's burden rises due to MRI activity relapse, a certain window for ideal treatment can also be determined for a particular therapeutic.

Figure 5:
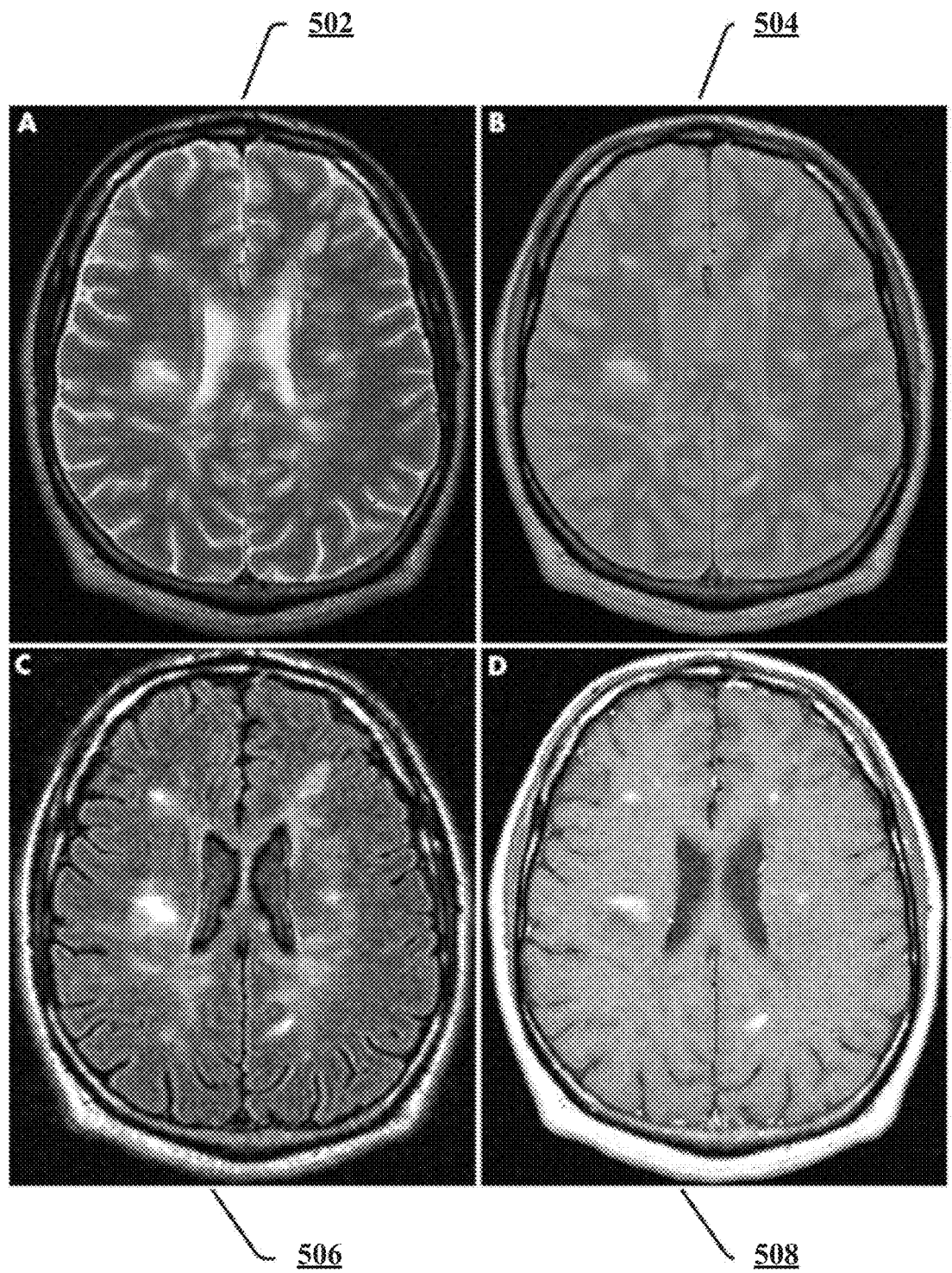
FIG. 5 illustrates an example of Magnetic Resonance Imaging (MRI) activity of a brain and lesions.

FIG. 5 illustrates an example of MRI activity and lesions. Magnetic resonance imaging (MRI) of the brain uses a magnetic field and radio waves to produce detailed images of the brain and the brain stem. MRI can detect a variety of brain conditions such as cysts, tumors, bleeding, swelling, developmental and structural abnormalities, infections, inflammatory conditions, or problems with the blood vessels. It can be used to detect damage to the brain caused by an injury or a stroke. Brain MRI's are also used to evaluate problems such as persistent headaches, dizziness and also detect chronic diseases of the nervous system such as multiple sclerosis. The need to identify the hidden relationship between symptoms and the brain imaging markers exists and may hold as the main factor to determine therapies. The MRI activity occurs during relapses to investigate the underlying pathophysiology of the relapse. Pathophysiology is the functional change that accompany a particular syndrome or a disease. A lesion is an area of tissue that has been damaged through injury or a disease. A brain lesion is an area of injury or a disease within the brain. Axial magnetic resonance imaging (MRI) of a patient with relapsing remitting multiple sclerosis (RR-MS) is shown. In this MRI, there are multiple periventricular lesions shown wherein, image 502 is a T2 weighted image, image 504 is proton density (PD) weighted image, image 506 is fluid attenuated inversion recovery (FLAIR) image and image 508 is a T1 weighted image following administration of gadolinium (Gd) demonstrating enhancing lesions. T2 weighted imaging identifies MS lesions as high signal foci against the low signal background of white matter. However, periventricular lesions are often indistinguishable from the adjacent CSF which is also of high signal with T2 weighting. By using PD weighting, contrast from the lesion can be improved because of the lower CSF signal with this sequence. T2 and PD weighted images can be acquired together in a single spin-echo sequence providing complimentary information. A problem of identifying lesions in the periventricular region, which is a common site for MS lesions, can also be addressed by suppressing the signal from CSF yet maintaining heavy T2 weighting using a fluid attenuated inversion recovery (FLAIR) sequence. This sequence is also superior at detecting cortical/juxtacortical lesions. FLAIR is a commonly used MR sequence on clinical scanners when MS has been raised as a possible clinical diagnosis. The need to illustrate medicine's current understanding of causes, progression and predicted therapeutic response to patients in the space of medical imaging is useful, since patients understand these lesions to be correlated with more troubling symptoms.

FIG. 6 illustrates an example flowchart 602 of a dual neural machine translation (d-NMT) algorithm that can be implemented using a processor 102 (FIG. 1) operatively coupled to memory 104 (FIG. 1). These embodiments use a dual neural machine translation (d-NMT) algorithmic core to train the parameterization of a generative model that employ sequences of medical records described by a disease progression model and translate these into an illustrative sequence of corresponding medical images using generated parameters of a mechanistic model. At 604, training parameterization of a generative model (e.g., using dual-neural machine translation algorithmic component 108) is accomplished by receiving sequences of medical records described by a disease progression model and translating the sequences of medical records to an illustrative sequence of corresponding images. The training is facilitated through acts 606, 608 and 610. At 606, a first future patient state and first medical record are predicted (e.g., using medical record prediction component 110) from a first sequence of medical records. At 608, a second future patient state and second medical image are predicted (e.g., using medical image prediction component 112) from a second sequence of medical images. At 610, a pathophysiological simulation is generated (e.g., using pathophysiological component 114) of a third future patient state using a third sequence of medical images given a first set of parameters wherein a first parameter reflects a population of patients that have presented a first type of medical record.

Figure 7:
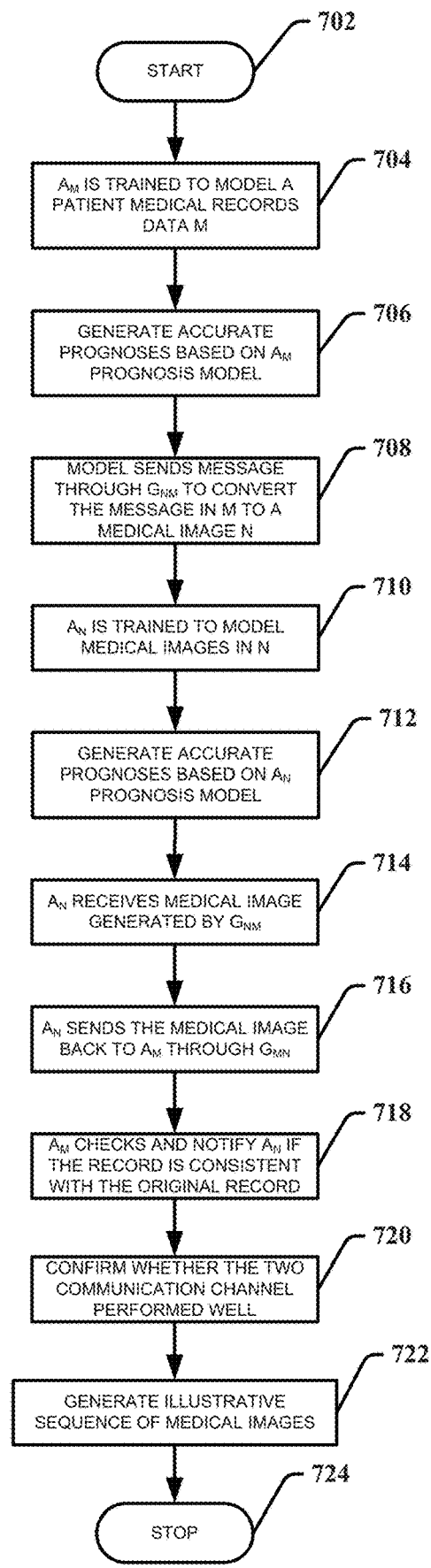
FIG. 7 illustrates an example flowchart of an implementation of a dual neural machine translation (d-NMT) algorithm in accordance with one or more implementations described herein.

FIG. 7 illustrates an example flowchart of the dual neural machine translation (d-NMT) algorithm. These embodiments use a dual neural machine translation (d-NMT) algorithmic core to train parameterization of a generative model that employs sequences of medical records described by a disease progression model and translates these into an illustrative sequence of corresponding medical images. The algorithm begins at block 702 by training patient record data M through first agent $A_M$ as denoted by block 704. This can produce accurate prognosis based on labels found in M and in agents prognosis model $\pi_M$ as denoted by block 706. This agent sends a message comprising a record in M to a second agent through a noisy channel known as the generative model $G_{NM}$ as denoted by block 708. This can convert the message in M into an illustrative medical image with some imaging modality N. Translation from M to N is achieved by parameterizing and running a physiological model and rendering the model's output as a medical image.

For example, a heart disease progression model action as $A_M$ produces an accurate prognosis from M. A parameters-generating model, $P_{NM}$, provides a second output vector from $A_M$, which is used to parameterize a heart model, $G_{NM}$. The heart model produces an echocardiogram in N which is provided to a second agent. The second agent, $A_N$, is trained to model medical images in N as denoted by block 710. It produces accurate prognosis based on certain labels provided to it and $A_{N'S}$ prognosis model, $\pi_N$ as denoted by block 712. $A_N$ receives the medical image in the modality N generated by $G_{NM}$ as denoted by block 714. It checks the generated image and notifies $A_M$ whether it's a natural image in the modality N. It is to be noted that the $A_N$ may not be able to verify the correctness of the translation from M to N since the original medical record is invisible to it. $A_N$ sends the received image back to the first agent through another noisy channel known as the generative model $G_{MN}$ as denoted by block 716. This converts the received medical image from modality N back to a medical record in M using another translation model.

It is to be noted that this translated output extends the original output vector of $A_N$ beyond the prognosis, which may already be in M, since $G_{MN}$ is tasked with modelling other medical record data that $A_N$ was not originally trained to model. For example, an echocardiogram reading model acting as $A_N$ produces an accurate prognosis from N. A parameters-generating model, $P_{MN}$, provides a second output vector from $A_N$, which is used to parameterize a medical record generator, $G_{MN}$. The medical record generator produces a complete medical record for the patient, which is then provided to the first disease progression model agent, $A_M$, for further analysis.

Upon receiving the medical record from the $A_N$, the first agent $A_M$ checks it and notifies the second agent whether the record it received is consistent with the original record sent as a message to $A_N$ as denoted by block 718. Through the feedback, both agents may know whether the two communication channels exchanged messages and analyze the two generative models' performance as denoted by block 720. For example, the heart disease progression model checks the record it receives and compares it to the original patient record. After training, GMN, becomes a useful illustrative Artificial Intelligence that can show a heart model to a cardiologist based only on a patient medical record. Thus, this algorithm can generate an illustrative sequence of medical images as denoted by block 722 and completes the method at block 724. The algorithm can also be started from the second agent $A_N$ with an original medical image in modality N, and then the two agents can go through a symmetric process and improve the two channels (generative models) according to the feedback received. Thus, repeating the process alternatively in either direction can improve the $G_{MN}$ performance and permit it to perform optimally as an illustrative AI. The algorithm is more formally presented below:

---

Algorithm 1 The dual-learning algorithm

1: Input: Medical records data, M, and medical imaging data, N, initial prognosis models $\pi_M$ and $\pi_N$, generative models $G_{NM}$ and $G_{MN}$, $\alpha$, generative search size K, learning rates $y_{1,t}, y_{2,t}$.
2: repeat
3:   t = t + 1.
4:   Sample medical record and medical image $s_M$ and $s_N$ from M and N respectively.
5:   Set s = $s_M$    /> Model update for the game beginning from M.
6:   Generate K medical images $s_1,..., s_K$ using physiological domain model according to parameters generating model
    P (.|s; $G_{NM}$).
7:   for k = 1,..., K do
8:     Set the parameters generating model reward for the kth sampled medical record as $r_{1,k} = \pi_N(s_K)$.
9:     Set the interpreter reward for the kth sampled sentence as
    $r_{2,k} = \log P(s/s_k; G_{MN})$.
10:    Set the total reward of the kth sample as $r_k = \alpha r_{1,k} + (1 - \alpha)r_{2,k}$.
11:   end for
12:   Compute the stochastic gradient of the parameters of $G_{NM}$:

$$\nabla_{G_{NM}} \hat{E}[r] = \frac{1}{K} \sum_{k=1}^{K} [r_k \nabla_{G_{NM}} \log P(s_k \mid s; G_{NM})].$$

13:   Compute the stochastic gradient of the parameters of $G_{MN}$:

$$\nabla_{G_{NM}} \hat{E}[r] = \frac{1}{K} \sum_{k=1}^{K} [(1 - \alpha)\nabla_{G_{MN}} \log P(s|s_k; G_{MN})].$$

14:   Model updates:
    $G_{NM} \leftarrow G_{NM} + y_{1,t}\nabla_{G_{NM}}\hat{E}[r], G_{MN} \leftarrow G_{MN} + y_{2,t}\nabla_{G_{MN}}\hat{E}[r]$.
15:   Set s = $s_N$    /> Model update for the game beginning from N.
16:   Go through line 6 to line 14 symmetrically.
17: until convergence

---

The algorithmic core of these embodiments comprises a disease progression model that operates on medical records to predict a subsequent patient state and medical record, and a disease progression model that operates on medical images to predict a subsequent patient state and medical images. These next-state-prediction models are termed as prognosis models and it acts in d-NMT similar to a language model in a standard d-NMT. By using a d-NMT algorithm, the advantages of the original algorithm concerning the removal of a dual corpus in both images and record scenario is leveraged here to obviate the need for having extensive corresponding data sets comprising medical records and medical images sampled synchronously from many patients.

Figure 8:
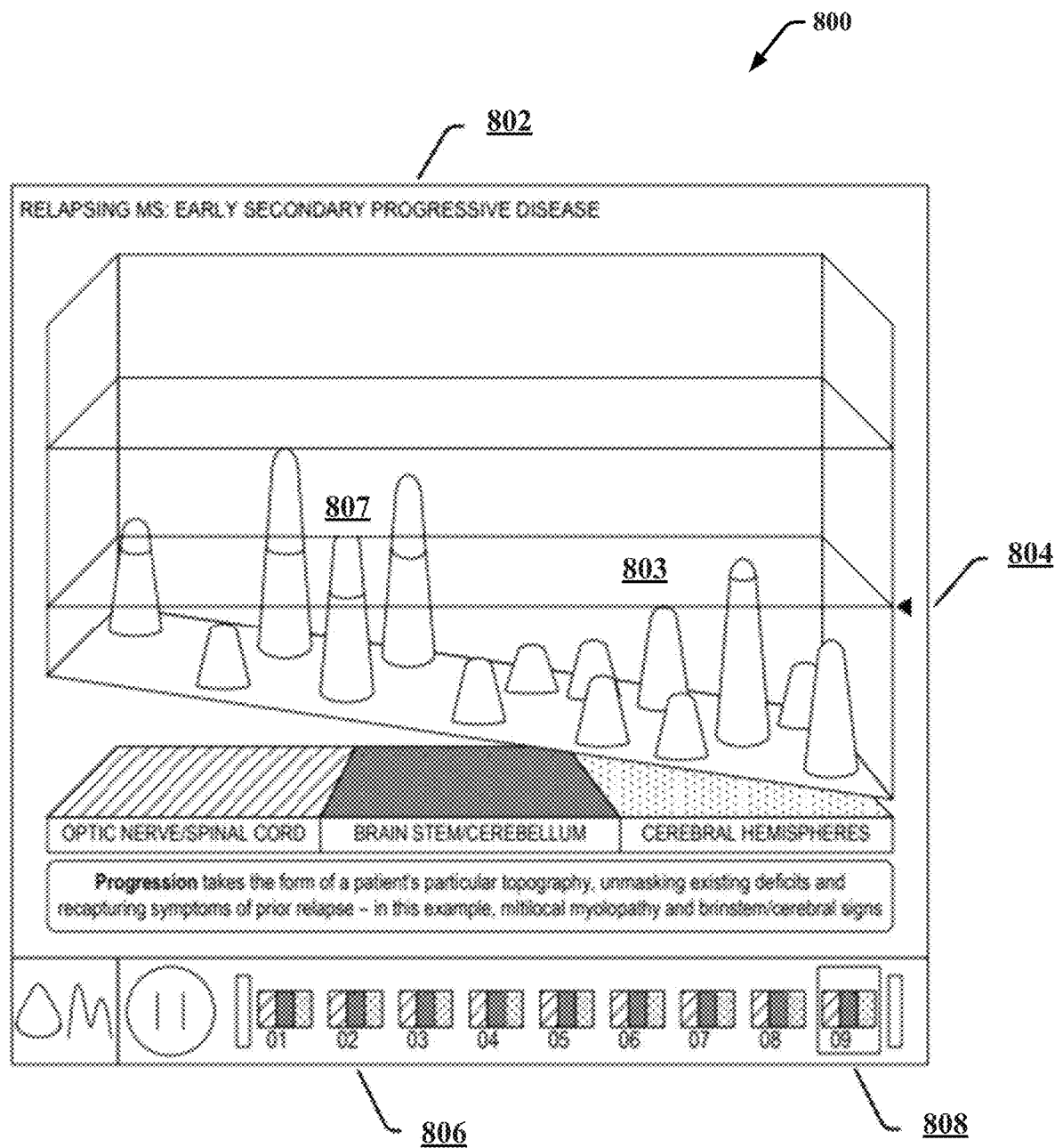
FIG. 8 illustrates an example of a leaking swimming pool model of relapsing-remitting multiple sclerosis (RR-MS) flare-ups in accordance with one or more implementations described herein.

FIG. 8 illustrates an example of a leaking swimming pool model of RR-MS flare-ups at year 1 and 9. A pathophysiological model 120 (FIG. 2) comprises a leaking swimming pool model as depicted through visualization 800. It is used in these embodiments as part of the d-NMT algorithm wherein it has several parameters and represents conditions for lesions and symptoms worsening by changing water levels, mound heights, and bottom slope in a swimming pool. A most common type of MS is a relapsing-remitting disease wherein a patient experiences flare-ups. During these flareups, the patient loses vision in one eye followed by periods of neurologic normalcy. The immune system has gone into overdrive when the flare-ups occur and then the activity subsides for months or even years. One method to explain these flare-ups is by using the swimming pool model. FIG. 8 depicts the visual representation 800 of how multiple sclerosis lesions and symptoms might progress over a period of time focusing on the events from years 1 to 9. As shown in block 802, a pool is shown with mountains rising high from the bottom. The mountains represent scars in the central nervous system and water surface 803 is a threshold at which symptoms appear as denoted by block 804. Lesions 807 below the water line do not cause symptoms whereas those jutting out of the water do. The water surface 803 can also be seen as the body's neurologic reserve capacity. Parts of the pool are sectioned by optic nerve/spinal cord, brainstem/cerebellum and cerebral hemispheres. At year 2 as denoted by block 806, lesions emerge as topographical peak which can be apparent on the MRI but have not crossed the initial clinical threshold. This depicts radiologically isolated syndrome (RIS).

As time progresses, the first lesion to cross the clinical threshold denotes the clinically isolated syndrome (CIS). Lesions in the shallow end are more likely to cross the threshold given less functional reserve in these regions. The emergence of subsequent subthreshold lesions defines relapsing-remitting multiple sclerosis (RR-MS) before a second clinical attack. The second clinical relapse defines clinically definite MS, such as in this example, a brainstem attack. Additional lesions denote ongoing disease activity. By year 9 as denoted by block 808, early secondary progressive MS(SPMS) is characterized by a rapid decline in the functional capacity, revealing the underlying lesion topography above the clinical threshold. This model shows lesions rising from a deep pool which represents the reserve capacity of the nervous system to withstand the disease.

In MS, the reserve capacity is changed depending on the level of stress in an individual's life. In this model, it is represented as a level of water in a time pool. The height of the lesions represents whether it is visible or systematic. In other words, if the mountains rise above the level of water, then it becomes visible on the MRI and can be linked with the symptoms. If the water level is rising up and down, then there is more or less of a chance of seeing a lesion which depends upon where in the pool the lesion is merged from and how high the peak is. Many of these parameters can be used to illustrate about a patient cycle of relapsing remitting MS. It may be even governed by a system of equations which is another way to animate this model and the parameters which govern the lesions height at different locations and the depth of the water can be used in a dynamic equation to predict the future in terms of where the lesions may have emerged and where the patient is going to have a problem. Some of those dynamic parameters can be indicated where the patient fits in the curve in a relapsing-remitting multiple sclerosis flare-up graph. In early stages, the pool parametrization that fits the patient's condition in the first part of the slope might involve a scalar that has a threshold associated with it. It is only when that scalar transforms through the nominee or model of the pool (CIS), it reaches the threshold where the window for an ideal treatment opens up. Thus, these mechanistic models and the models that can capture pathophysiology are preferred to be used to reveal the underline pathophysiological thresholds for a treatment. In this way, the patient's level of metabolic stress in the tissue can be identified to indicate whether a patient has critical MS.

Human brains are astoundingly resilient that if one part of the brain is injured, neighboring neurons can step in and take over. However, as a patient ages and MS progresses, not only does the lesioning worsen, which in this case means the mountains grow higher, but the brain also loses its ability to compensate for injured tissue. In the swimming pool model, the water starts draining out of the pool and more lesions and resulting symptoms become apparent. Infirmity is driven here principally by dropping of the threshold or the surface level. Progression employs the form of a patient's particular disease topography, unmasking existing deficits and recapitulating symptoms of prior relapse, in the model described in the section above, multifocal myelopathy and brainstem/cerebellar signs appear as years progress. Relapsing-remitting patients have mountains that temporarily rise above the waterline but then sink again. Formally linking sound machine learning-based progression models of RR-MS to predictions of likely lesion progression using a modified d-NMT system benefits the patients and doctors in deciding among many therapeutic options. This illustration of underlying pathophysiology and its dynamics is used to inform patients about the complexity of this disease and what they might expect hypothetically. These embodiments couple this model to a real-world evidence-based prediction of patient symptoms (e.g., medical records) with the illustration acting to predict medical images. Hidden pathophysiological relevant parameters of the optimized model become an input to a therapeutic determining module. These embodiments mainly focus on creating a system that learns a category, reconstructs an image based on a mechanistic model and combines a machine learning latent space with the parameters of a mechanistic model.

Figure 9:
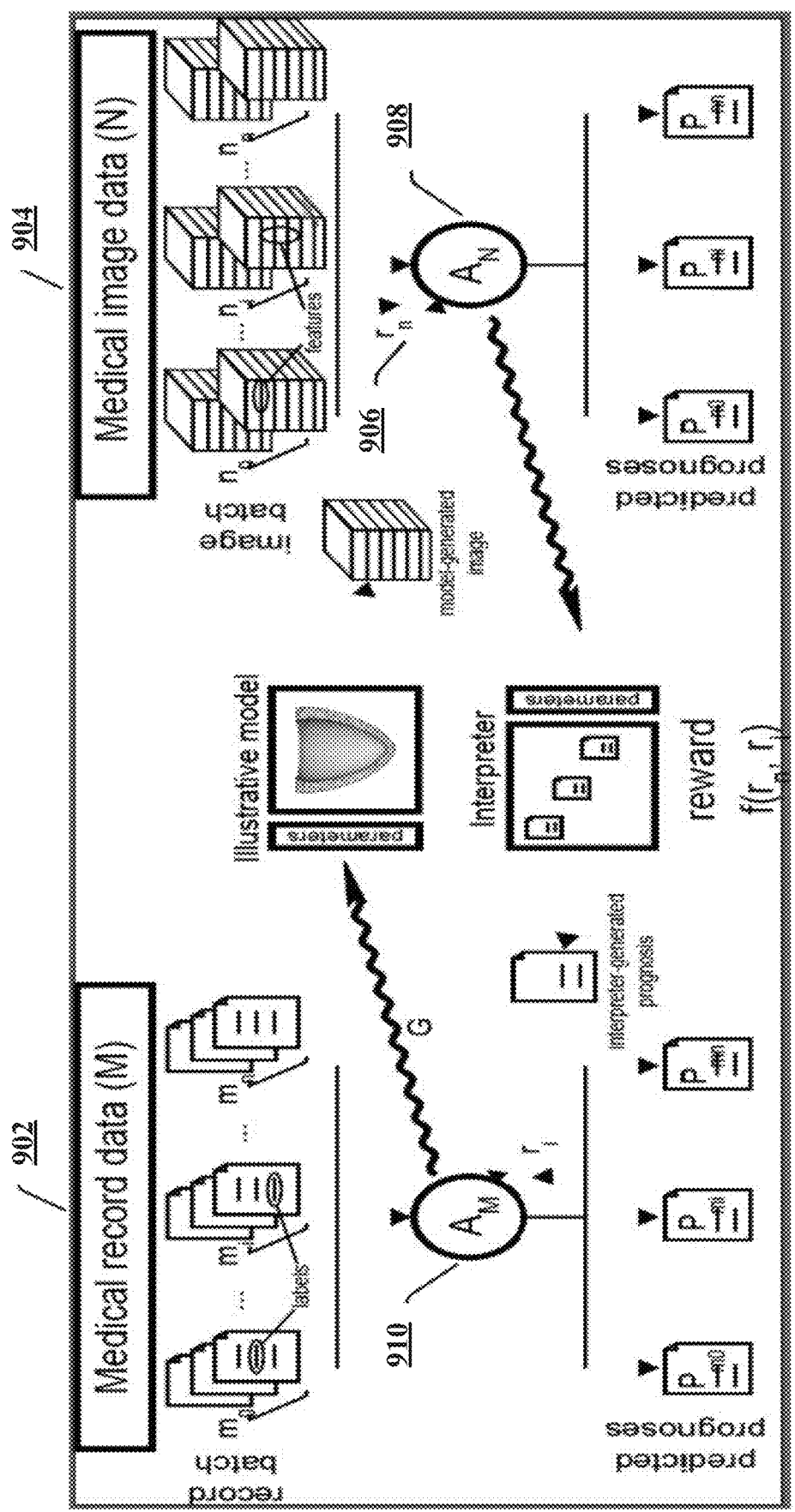
FIG. 9 illustrates an example of a translation model in accordance with one or more implementations described herein.

FIG. 9 illustrates an example of a translation model. This problem can be viewed as a machine translation problem. In this model, given the last three medical records, the next medical record can be predicted as denoted by block 902. Similarly, given the last three medical images, the next medical image can be predicted as denoted by block 904. Using dual neural machine translation, given three medical records the generative model can produce three medical images and vice versa. This is a mechanistic model where models can be imaged as if it were real tissues. The advantage of this method is that a dual corpus may not be required to learn the translation, such that the algorithm does not need to learn examples to generate the result and can provide a way to evaluate the quality of the translation independent of the dual corpus. An $r_n$, as denoted by block 906, is a reinforcement learning signal that is used to change the generative model. It can identify an invalid translation such that the model is improved based on that signal. There is one other reinforcing signal wherein a generative model can translate medical images to medical records and this is used as a black box (diagnosis model). Upon completing the round-trip of translating medical records to medical images and then back to medical record data, the return signal can be compared to the original message to check if the information is the same.

Hence, with these two enforcing signals, these embodiments facilitate the discovery of a set of mechanistic parameters used to translate medical records to medical images through a mechanistic model and support the discovery using the algorithm to discover a set of parameters which are pathophysiological. The parameters are real pathophysiological parameters of a mechanistic model, wherein a set of parameters are sampled from a distribution of parameters which reflects the population of patients to have presented a medical record of this type. The two adversarial components for training are combined wherein the first adversarial component is $G_{MN}+A_N$ and the second adversarial component is $G_{NM}+A_M$. GAN training can be modified to accommodate both of the rewards generated by $A_N$ as denoted by block 908 and $A_M$ as denoted by block 910 into loss functions $G_{MN}$ and $G_{NM}$. In other words, the loss functions of the generative models (e.g., illustrative model and interpreter) may account and penalize those generated medical images and reports that are not recognized as believable by $A_N$ and $A_M$ respectively. Total reward of the system at sample t: $r_t=(a\ r_{1t}+b\ r_{2t})+$"discounted future". Standard deep reinforcement learning algorithms such as Q-learning can be used to estimate gradients of the loss function and update the parameters $p_{NM}$ and $p_{MN}$ of the illustrative model $G_{MN}$ and interpreter $G_{NM}$. Training of $G_{MN}$ and $G_{NM}$ proceeds by penalizing mismatches between the input data and outcome of the dual process. In other words, the equation below can be exploited such that:

$$P(M)P(N|M,\ p_{NM})=P(N)P(M|N,\ p_{MN})$$

where $p_{NM}$ and $p_{MN}$ are the parameters of the illustrative model $G_{MN}$ and the interpreter $G_{NM}$ respectively. M is the medical record and N is the medical imaging data. The constraint on the combined probability can be converted into penalty terms of the loss functions for $G_{MN}$ and $G_{NM}$ which are then handled with a method of Lagrange multipliers.

There are subtleties in the data that are constrained through optimization for learning a pathophysiological model and specific parameters are required to replicate medical imaging data, and those specific parameters can be evaluated for a likely response to a medication directly because they include pathophysiological parameters. For example, there are measures of ion channels among tissue components which act as priors on model parameters. Note that the pathophysiological model has the property of not being able to learn it using gradient descent. It is a system of equation that represents tissues, like contracting hearts or neurophysiology and metabolic stress, and those are not differentiated when compared to the black box model that uses gradient descent and is directly differentiable. One way to distinguish the pathophysiological model from a black box model is using an example from a traditional medical examination. Given a medical image and subject to a type of translation learning and being able to determine the likely smoking status of the patient (medical record) is the translation model. These embodiments can translate medical records to a sequence of medical images. Similarly, it can employ a sequence of medical images and produce a translation of the images into a sequence of medical records. It does this through a generative interpreter model that has several parameters and can be used to input patient medical record measurements that were not taken and lead to informed follow up on these by doctors to assist with therapeutic endpoint measures. In both generative models, the parameters of the model are learned by a reinforcement learning algorithm based on the quality of the forward medical image sequence generated (e.g., whether the medical image prognosis model can process it) and the quality of the round-trip (e.g., whether the medical record sequence returned by the generative interpreter matches the original sequence). Because they correspond to pathophysiological measures, these inferred parameters are ideal to be used by a therapeutic determining module to recommend therapies, doses, and time courses. The core also comprises a generative model that can produce a pathophysiological simulation of a patient state given a medical record to produce a sequence of medical images, and an interpretation of a medical image and simulation of a patient state to produce a sequence of medical records. In particular, a therapeutic determining module uses the parameters optimized for the patient from the two generative models as an input to a therapy, dose, and time course selection.

Figure 10:
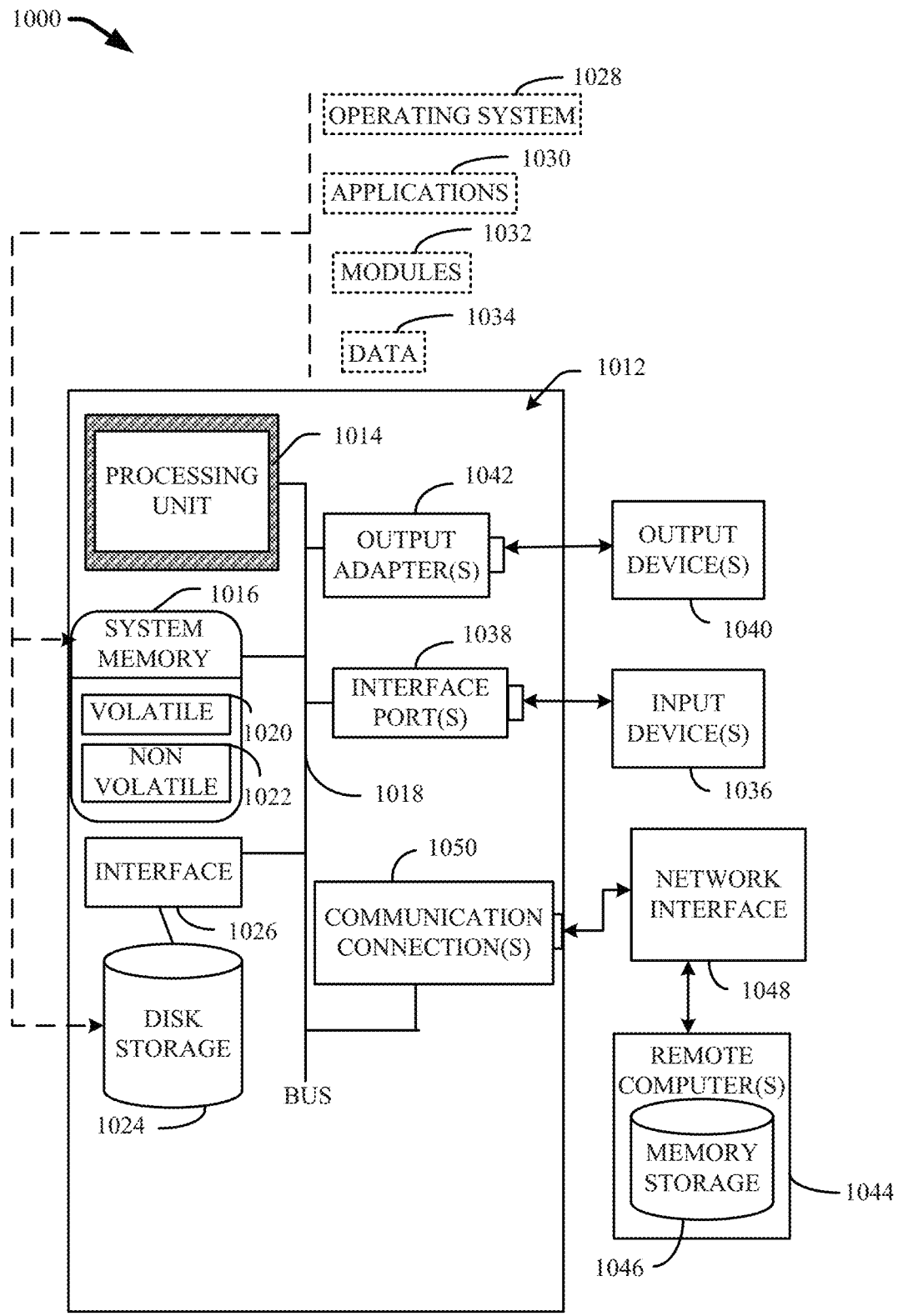
FIG. 10 illustrates a schematic diagram of an example operating environment in accordance with one or more implementations described herein.

FIG. 10 illustrates a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1094), and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random-access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a means of connection between the output device 1040 and the system bus 1018. It can be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor-based appliance, a peer device or other common network node and the like, and typically can also include many or the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in one or more computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, to perform aspects of the present invention.

Aspects of the present invention are described herein with reference to flowchart illustrations and/or block diagrams of methods, apparatus (systems), and computer program products according to embodiments of the invention. It can be understood that one or more blocks of the flowchart illustrations and/or block diagrams, and combinations of blocks in the flowchart illustrations and/or block diagrams, can be implemented by computer readable program instructions. These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, one or more blocks in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It can also be noted that one or more block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art can recognize that this disclosure also can or can be implemented in combination with other program modules. Generally, program modules include routines, programs, components, data structures, etc. that perform particular tasks and/or implement abstract data types. Moreover, those skilled in the art can appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not many aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a server computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings may generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random-access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products, and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A system, comprising:
a processor, operatively coupled to a memory, that executes the following computer executable components:
a dual-neural machine translation algorithmic component that trains parameterization of a generative model by receiving sequences of medical records described by a disease progression model and translates the sequences of medical records to an illustrative sequence of corresponding images, wherein the training is performed using the following computer executable components:
a medical record prediction component that predicts a first future patient state and first medical record from a first sequence of medical records;
a medical image prediction component that predicts a second future patient state and first medical image from a first sequence of medical images; and
a pathophysiological component that generates a pathophysiological simulation of a third future patient state using a second sequence of medical images given a first set of parameters wherein a first parameter reflects a population of patients that have presented a first type of medical record.

2. The system of claim 1, further comprising an interpreter component that generates a second sequence of medical records given a second set of parameters wherein a second parameter reflects a population of patients that have presented a first type of medical image.

3. The system of claim 1, further comprising a translation model that interprets a second sequence of medical records described by the generative model and translates the second sequence of medical records into the illustrative sequence of corresponding medical images.

4. The system of claim 1, wherein the training is facilitated using a pathophysiological model that comprises a leaking swimming pool model.

5. The system of claim 1, further comprising a generative component that employs a second set of parameters to impute patient medical record measurements that were not considered in an evaluation and generate a follow-up notification on these records to assist with therapeutic endpoint measures.

6. The system of claim 4, further comprising a generative component that selects records based on learned parameters of a reinforcement learning algorithm by quality of a forward medical image sequence and round-trips.

7. The system of claim 1, further comprising a therapeutic component that uses parameters optimized for a patient from a set of generative models as inputs to therapy, dose, and time course selection.

8. A computer-implemented method, comprising:
using a processor, operatively coupled to a memory, to execute computer executable components to perform the following acts:
using the processor to train parameterization of a generative model by receiving sequences of medical records described by a disease progression model and translates the sequences of medical records to an illustrative sequence of corresponding images, wherein the training is performed by:
using the processor to predict a first future patient state and first medical record from a first sequence of medical records;
using the processor to predict a second future patient state and first medical image from a first sequence of medical images; and
using the processor to generate a pathophysiological simulation of a third future patient state using a second sequence of medical images given a first set of parameters wherein a first parameter reflects a population of patients that have presented a first type of medical record.

9. The method of claim 8, further comprising using the processor to generate a second sequence of medical records given a second set of parameters wherein a second parameter reflects a population of patients that have presented a first type of medical image.

10. The method of claim 8, further comprising using the processor to interpret a second sequence of medical records described by the generative model and translates the second sequence of medical records into the illustrative sequence of corresponding medical images.

11. The method of claim 8, further comprising using the processor to facilitate the training by employing a pathophysiological model that comprises a leaking swimming pool model.

12. The method of claim 8, further comprising using the processor to employ a second set of parameters to impute patient medical record measurements that were not considered in an evaluation and generate a follow-up notification on these records to assist with therapeutic endpoint measures.

13. The method of claim 11, further comprising using the processor to select records based on learned parameters of a reinforcement learning algorithm by quality of a forward medical image sequence and round-trips.

14. The method of claim 8, further comprising using the processor to use parameters optimized for a patient from a set of generative models as inputs to therapy, dose, and time course selection.

15. A computer program product comprising a computer readable storage medium having program instructions embodied therewith, the program instructions executable by a processor to cause the processor to:

train, using the processor, parameterization of a generative model by receiving sequences of medical records described by a disease progression model and translates the sequences of medical records to an illustrative sequence of corresponding images, wherein the training is performed by:

predicting, using the processor, a first future patient state and first medical record from a first sequence of medical records;

predicting, using the processor, a second future patient state and first medical image from a first sequence of medical images; and generating, using the processor, a pathophysiological simulation of a third future patient state using a second sequence of medical images given a first set of parameters wherein a first parameter reflects a population of patients that have presented a first type of medical record.

16. The computer program product of claim 15, further comprising generating, using the processor, a second sequence of medical records given a second set of parameters wherein a second parameter reflects a population of patients that have presented a first type of medical image.

17. The computer program product of claim 16, further comprising interpret, using the processor, a third sequence of medical records described by the generative model and translates the third sequence of medical records into the illustrative sequence of corresponding medical images.

18. The computer program product of claim 15, further comprising facilitate the training, using the processor, by employing a pathophysiological model that comprises a leaking swimming pool model.

19. The computer program product of claim 15, further comprising employ, using the processor, a second set of parameters to impute patient medical record measurements that were not considered in an evaluation and generate a follow-up notification on these records to assist with therapeutic endpoint measures.

20. The computer program product of claim 15, further comprising selecting, using the processor, records based on learned parameters of a reinforcement learning algorithm by quality of a forward medical image sequence and round-trips.

* * * * *